US009874619B2

(12) United States Patent
Green

(10) Patent No.: US 9,874,619 B2
(45) Date of Patent: Jan. 23, 2018

(54) METHODS FOR PERFORMING NMR MEASUREMENTS ON POROUS MEDIA

(71) Applicant: Green Imaging Technologies, Inc., Fredericton (CA)

(72) Inventor: Derrick Green, Fredericton (CA)

(73) Assignee: Green Imaging Technologies, Inc., Fredericton, NB (CA)

( * ) Notice: Subject to any disclaimer, the term of this patent is extended or adjusted under 35 U.S.C. 154(b) by 974 days.

(21) Appl. No.: 14/226,189

(22) Filed: Mar. 26, 2014

(65) Prior Publication Data

US 2014/0203807 A1 Jul. 24, 2014

Related U.S. Application Data

(63) Continuation of application No. 12/893,510, filed on Sep. 29, 2010.

(51) Int. Cl.
   *G01R 33/44* (2006.01)
   *G01N 24/08* (2006.01)
   *G01V 3/32* (2006.01)
   *G01R 33/46* (2006.01)

(52) U.S. Cl.
   CPC .......... *G01R 33/44* (2013.01); *G01N 24/081* (2013.01); *G01R 33/448* (2013.01); *G01V 3/32* (2013.01); *G01R 33/4625* (2013.01)

(58) Field of Classification Search
   CPC .. G01R 33/44; G01R 33/448; G01R 33/4625; G01N 24/081; G01V 3/32
   See application file for complete search history.

(56) References Cited

U.S. PATENT DOCUMENTS

| 5,796,252 | A * | 8/1998 | Kleinberg | G01V 3/32 324/303 |
| 6,462,542 | B1 * | 10/2002 | Venkataramanan | G01N 24/081 324/300 |
| 6,597,171 | B2 * | 7/2003 | Hurlimann | G01N 24/081 324/300 |
| 6,605,943 | B1 * | 8/2003 | Clark | G01R 33/50 324/309 |
| 6,937,013 | B2 * | 8/2005 | Ganesan | G01V 3/32 324/303 |
| 7,053,611 | B2 * | 5/2006 | Freedman | G01V 3/32 324/300 |
| 7,532,007 | B2 * | 5/2009 | Song | G01V 3/32 324/303 |
| 7,683,618 | B2 * | 3/2010 | Balchandani | G01R 33/4833 324/307 |

(Continued)

OTHER PUBLICATIONS

Lalitha et al. "Solving Fredholm Integrals of the First kind with tensor product structure in 2 and 2.5 dimensions", May 2002, IEEE pp. 1017-1026.*

(Continued)

*Primary Examiner* — Dixomara Vargas
(74) *Attorney, Agent, or Firm* — Eugene F. Derényi; Fogler, Rubinoff LLP

(57) ABSTRACT

NMR measurements and methods of analyzing those measurements are disclosed. A single NMR measurement is performed then that data is analyzed. Additional NMR measurements are performed and analyzed sequentially then the array of NMR analyzed data is analyzed again to get information about the system under study.

13 Claims, 4 Drawing Sheets

(56) References Cited

U.S. PATENT DOCUMENTS

| | | | | |
|---|---|---|---|---|
| 8,427,145 B2* | 4/2013 | Mitchell | ............ | G01N 24/081 |
| | | | | 324/303 |
| 8,547,090 B2* | 10/2013 | Lukin | ............ | G01R 33/032 |
| | | | | 324/244.1 |
| 8,565,854 B2* | 10/2013 | Bryskhe | ............ | A61B 5/055 |
| | | | | 324/307 |
| 8,723,519 B2* | 5/2014 | Boulant | ............ | G01R 33/446 |
| | | | | 324/307 |
| 8,754,644 B2* | 6/2014 | Trakic | ............ | G01R 33/5659 |
| | | | | 324/307 |
| 8,810,244 B2* | 8/2014 | Topgaard | ............ | G01R 33/56341 |
| | | | | 324/309 |
| 9,599,688 B2* | 3/2017 | Grunewald | ............ | G01V 3/14 |
| 2002/0067164 A1 | 6/2002 | Venkataramanan et al. | | |
| 2003/0169040 A1 | 9/2003 | Hurlimann et al. | | |
| 2006/0272812 A1 | 12/2006 | Yu et al. | | |

OTHER PUBLICATIONS

Mitchell J et al.: "Nuclear Magnetic Resonance Relaxation and Diffusion in the Presence of Internal Gradients: The effect of magnetic field strength", Physical Review E, vol. 81, No. 2, Feb. 1, 2010, pp. 26101-1 XP007920234.

Extended European Search Report dated Feb. 17, 2012 issued on European Patent Application No. 11182957.8.

M. C. Leverett.: "Capillary Behaviour in Porous Solids", Petroleum Technology, T.P. 1223, A.I.M.E Tulsa Meeting, Oct. 1940, pp. 152-169.

Harry W. Brown.: "Capillary Pressure Investigations", Petroleum Transactions, AIME. vol. 192, 1951, pp. 67-74.

M. TH. Van Genuchten.: "A closed-form Equation for Predicting the Hydraulic Conductivity of Unsaturated Soils", Soil Sci. Soc. Am. J., vol. 44, 1980 pp. 892-898.

R. H. Brooks & A.T. Corey.: "Hydraulic Properties of Porous Media", Hydrology Papers, Colorado State University—Mar. 1964, pp. 1-37.

G. I Hassler & E. Brunner.: "Measurement of Capillary Pressures in Small Core Samples", Petroleum Technology T.P. 1817, Member A.I.M.E. Los Angeles Meeting, Oct. 1944, pp. 114-123.

N. T. Burdine.: "Relative Permeability Calculations From Pore Size Distribution Data" Petroleum Transactions, The Log Analyst, AIME vol. 198, 1953, pp. 71-77.

Douglas E. Ruth & Zhigang Andy Chen.: Measurement and Interpretations of Centrifuge Capillary Pressure Curves—The SCA Survey Data,The Log Analyst, Sep.-Oct. 1995, pp. 21-33.

* cited by examiner

METHODS FOR PERFORMING NMR MEASUREMENTS ON POROUS MEDIA

CROSS-REFERENCE TO RELATED APPLICATIONS

This application claims the benefit of U.S. application Ser. No. 12/893,510, which is pending as of the time of filing.

FIELD

The present invention relates to nuclear magnetic resonance ("NMR") measurements and their analysis.

BACKGROUND

NMR is a common laboratory and field tool used throughout many industries. One example is the oil industry which uses NMR to analyze the content and environment of water, oil, and gas in porous media like subterranean reservoir rock.

In general, NMR detects the amount of hydrogen (for proton NMR) in a sample or object under study. The lifetime of the detected NMR signal depends on the environment of the hydrogen. For example, an NMR signal detected from hydrogen in oil generally decays faster than an NMR signal detected from hydrogen in free water. In oil field application, differences in the rate of decay of NMR signals can be used to distinguish among for example, oil, water and gas in rock.

NMR signal decay times can also be used to distinguish among clay bound ("CBW"), capillary bound ("BVI") and free fluid ("FFI") quantities in reservoir rock.

A common method to determine CBW, BV1 and FFI quantities is to use either $T_2$ or $T_1$ relaxation times. The NMR relaxation parameters $T_1$ and $T_2$ are known by those skilled in the art to follow the following equations:

$$\frac{1}{T_2} = \frac{1}{T_{2-Bulk}} + \rho \frac{S}{V} + (\gamma GT_E)^2 \frac{D_o}{12} \quad (1)$$

$$\frac{1}{T_1} = \frac{1}{T_{1-Bulk}} + \rho \frac{S}{V} \quad (2)$$

where $\rho$ is the relaxometry constant, $D_o$ is the free diffusion constant for the fluid, $\gamma$ is the gyro magnetic ratio, G is the internal field gradient, TE is the echo time (a measurement parameter), and SN is the surface to volume ratio of the pores.

Equations (1) and (2) above reduce to direct relationships to the surface to volume ratio due to the fact that, in rocks, the bulk relaxation times are much longer than the measured values and typically, an echo time (TE) is selected such that the diffusion term can be ignored. The surface to volume ratio is a measure of the pore size distribution of the rock being studied.

The relaxation parameters $T_1$ and $T_2$ can be measured using many different NMR measurement pulse sequences known to those skilled in the art. For example, for $T_2$ analysis, a prior art CPMG sequence can be used (see FIG. 1) and for $T_1$ analysis, a prior art inversion recovery sequence can be used (see FIG. 2), where RF is the radio frequency excitation pulses, Tau is a delay time equal to ½ the echo time (TE) and ACQ is acquired NMR signal.

A problem with the above method is that if there is more than one fluid in the porous media being analysed (e.g. subterranean reservoir rock), the results no longer follow the simple equations 1) and 2) above. This makes the results difficult, if not impossible, to interpret.

SUMMARY

According to one or more aspects of the disclosed subject matter, a method is described for providing information about a system under study by performing two or more NMR measurements, varying a NMR measurement parameter between these measurements, analyzing each of the measurements separately, then reordering and analyzing the data at each variation used across the measurements.

According to one or more aspects of the disclosed subject matter, a method is described for extracting information about a system (the system can be a porous media such as rock) comprising performing a NMR measurement; acquiring NMR data from the measurement (the data can be a decaying signal dependent on the relaxation parameter $T_2$); expressing the NMR data using a kernel of one dimension; and analyzing the data to extract information (the information extracted can be the NMR relaxation parameter $T_2$). The analysed data can be presented (such on a computer screen display) in the form of a two dimensional map or image.

These steps can be repeated a sufficient number of times to acquire a sufficient amount of data in three or more dimensions, systematically changing one variable (the variable can be the NMR relaxation parameter $T_1$ or the molecular diffusion coefficient) to modify the NMR data with each repeat. The acquired data can then be reordered to form a one dimensional kernel across the systematically changed variable. The data can then be analyzed to extract information (the information extracted can be then be dependant on both $T_2$ and $T_1$ (or Diffusion)). The acquired NMR data can be compressed and the compressed NMR data can be analyzed using a Butler-Read-Dawson optimization method.

According to one or more aspects of the disclosed subject matter, a method is described for performing a NMR measurement on a porous media wherein at least one NMR measurement parameter is used; obtaining a decay signal from the media based on the NMR measurement parameter; altering one of the at least one NMR measurement parameter and repeating these steps. The decay signal can be dependent on the relaxation parameter $T_2$. The at least one NMR measurement parameter can be selected from the group consisting of a NMR relaxation parameter T2, a NMR relaxation parameter T1 and a molecular diffusion coefficient. Data can be obtained from the decay signal. The data obtained can depend on one or more of the NMR parameters from the group consisting of the NMR relaxation parameter $T_1$, NMR relaxation parameter $T_2$ and the molecular diffusion coefficient. Steps in the method can be repeated to 3 more dimensions.

DETAILED DESCRIPTION

Figure 3:
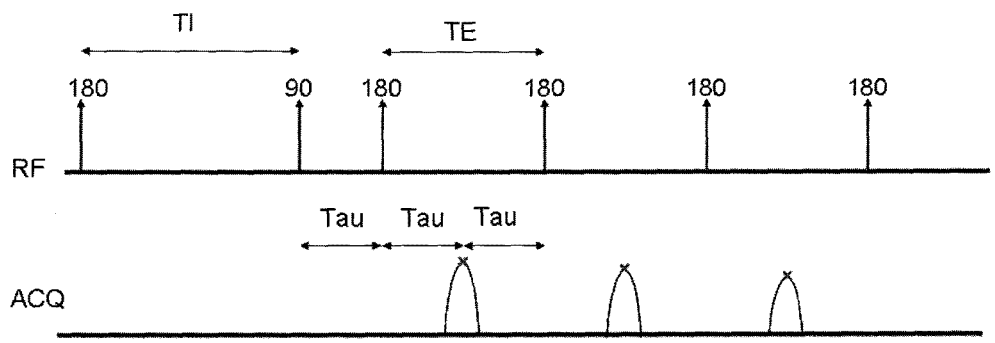
FIG. 3 is a diagram of a prior art inversion recovery CPMG sequence.

Referring to FIG. 3, a NMR measurement inversion recovery CPMG sequence can be used to acquire a plurality of NMR measurements and to systematically vary an NMR measurement parameter, in this case the delay time, $T_1$. The number of NMR measurements made will vary depending upon the requirement to have enough data and the duration of the measurement period. Suitable conventional NMR signal acquisition equipment can be used to make the NMR measurements. It will be understood by those skilled in the art that other prior art pulse sequences can also be used for the same purpose.

After each NMR measurement in a plurality of NMR measurements, the decaying NMR signal, S(t), obtained is related to the following equation:

$$S(t) = \sum_{i=1}^{N} A(i) e^{-\frac{t}{T_2(i)}} \quad (3)$$

Equation (3) can be solved by minimizing the following equation:

$$\text{Error} = \sqrt{\sum_{t=TE}^{t=j*TE}\left(m(t) - \sum_{i=1}^{N} A(i)e^{-\frac{t}{T_2(i)}}\right)^2} + \alpha \sqrt{\sum_{i=1}^{N} A(i)^2} \quad (4)$$

where A(i) is the amplitude of each exponential decay component, $T_2(i)$, t is time, TE is the CPMG echo time, N is the number of exponential decay components, and $\alpha$ is a smoothing coefficient used in the fitting. This equation can be rewritten to use a kernel of:

$$\text{Kernel}(t, T2(i)) = e^{-\frac{t}{T_2(i)}} \quad (5)$$

This simplifies the error Equation (4) to:

$$\text{Error} = \sqrt{\sum_{t=TE}^{t=j*TE}\left(m(t) - \sum_{i=1}^{N} A(i)\text{Kernel}(t, T_2(i))\right)^2} + \alpha \sqrt{\sum_{i=1}^{N} A(i)^2} \quad (6)$$

The advantage of using a kernel is that it simplifies computation in a computer algorithm. It will be understood by those skilled in the art that computational aspects of the present invention can be computer implemented and performed using a general purpose computer programmed for the purpose. The method of one or more embodiments of the present invention can be stored on non-transitory computer readable memory (such as but not limited to CDs, hard drives, and memory sticks) as statement and instructions for execution by a computer to carry out the method.

Figure 1:
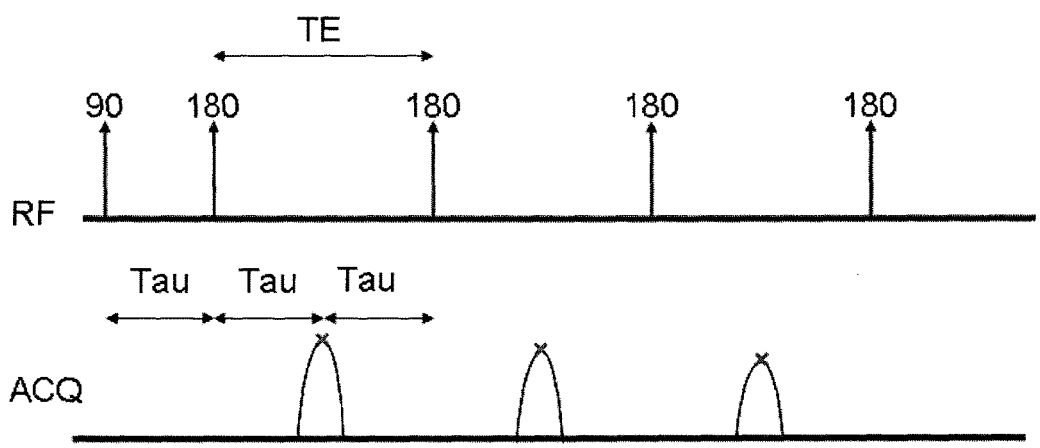
FIG. 1 is a representative diagram of a prior art CPMG sequence for $T_2$ analysis.
Figure 2:
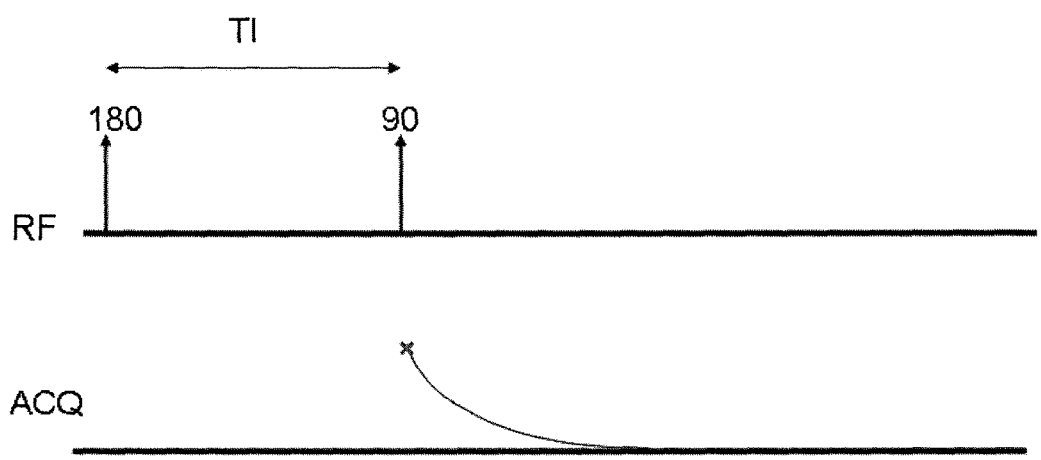
FIG. 2 is a representative diagram of a prior art inversion recovery sequence for $T_1$ analysis.

Upon completion of the plurality of NMR measurements and relating the resulting data to Equation (3), the data is reordered into a series of one dimensional ("1D") datasets In one embodiment, the first point in each analyzed data set forms the first reordered dataset. These reordered datasets are analyzed one by one using the known equation representing the pulse sequence that created by the variation in NMR measurement parameter. In the case of the pulse sequence shown in FIG. 2 this equation is:

$$S(t) = \sum_{i=1}^{N} A(i)\left(1 - 2e^{-\frac{t}{T_1(i)}}\right) \quad (7)$$

Figure 4:
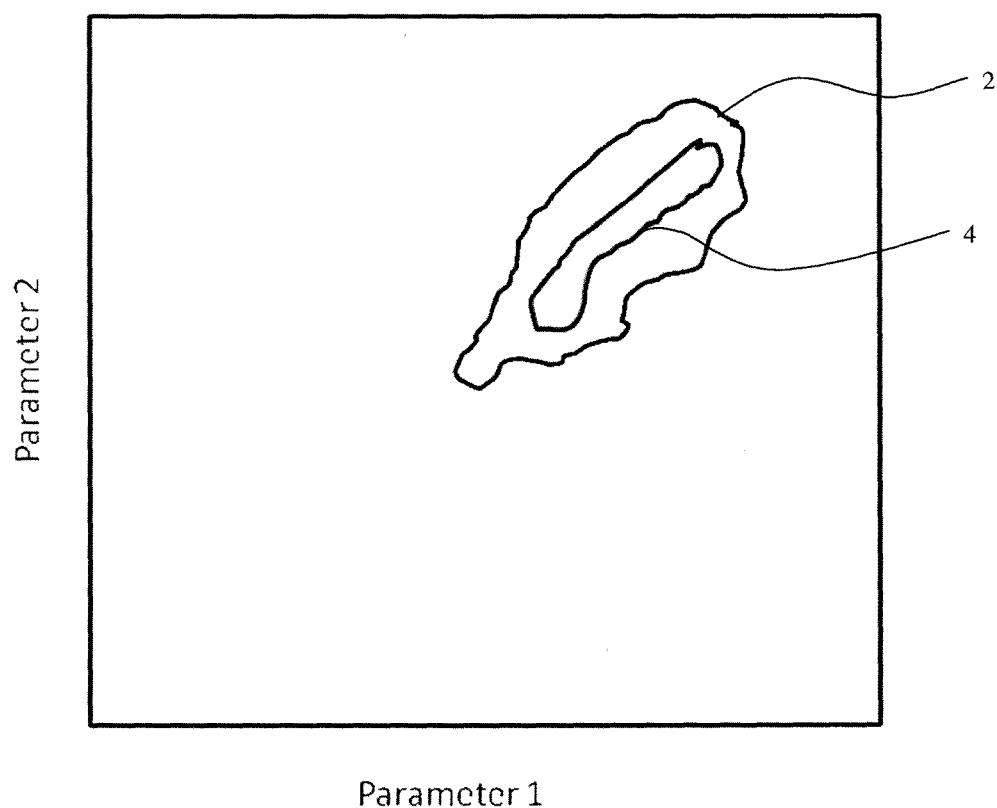
FIG. 4 is a diagram of a two dimensional map of a final result of the method according to the present invention.
Figure 5:
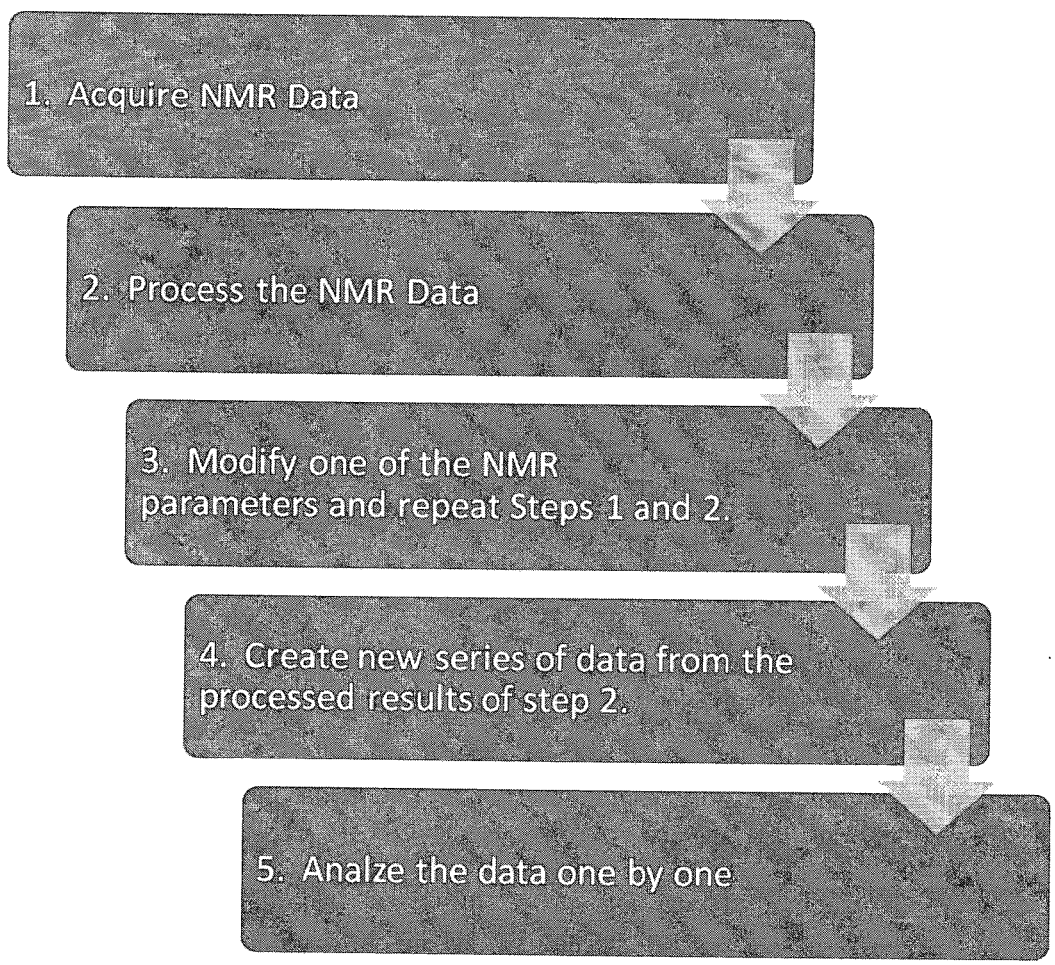
FIG. 5 is a flow diagram of steps according to one or more embodiments of the present invention.
Figure 6:
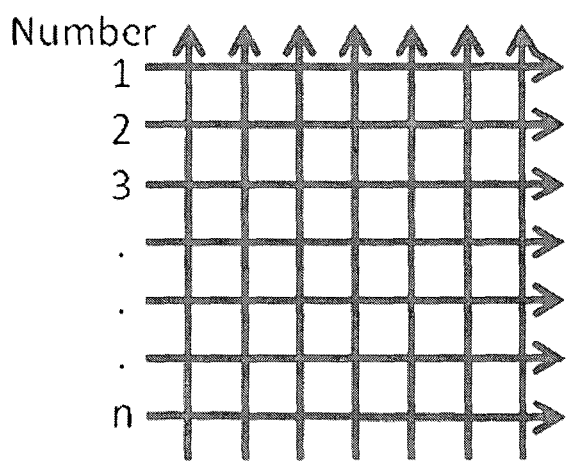
FIG. 6 is a schematic diagram of 1D processing steps according to one or more embodiments of the method of the present invention.

The resultant data obtained by solving equation (S) forms a two dimensional ("2D") result which can be analyzed to look for differences in the parameters in Equation (1) at different values from Equation (2). See FIG. 4 for an example of the result. In this schematic contour plot representation of a result, the resultant value is converted into an image intensity and plotted at an x-y coordinate equal to the parameter from equation (1) and the parameter from Equation (2). The two contour lines 2 and 4 in the image represent different image intensities. While in this example, the $T_2$ parameter is used for the 1st dimension and $T_1$ for the second dimension, this can be reversed. The flow diagram of FIG. 5 shows steps of one more embodiments of a method according to the present invention. The diagram in FIG. 6 shows the number of 1D processing steps depicted by the arrows. Note that the order of the processing is unimportant as long as all the horizontal processing steps are completed before the vertical steps (or vice versa). In the example above the horizontal processing steps are the solutions to Equation (1) and the vertical are the solutions to Equation (2).

What is claimed is:

1. A computer-implemented method of extracting information about a porous medium comprising:
   a. performing a NMR measurement on the porous medium, wherein performing the NMR measurement comprises the use of at least one NMR variable;
   b. acquiring NMR data from the measurement;
   c. expressing the NMR data using a kernel of one dimension;
   d. extracting a parameter of the porous medium from the data;
   e. repeating steps a. through d., changing one of the NMR variables each time steps a. through d. are repeated;
   f. reordering data obtained from step e. to form a one-dimensional kernel across the systematically changed variable in step e, and
   g. analyzing the data from step f. to a parameter of the porous medium from the data.

2. The method of claim 1 further comprising compressing the NMR data.

3. The method of claim 2 wherein the compressed NMR data are analyzed using a Butler-Read-Dawson optimization method.

4. The method of claim 1 wherein the analyzed data is presented in the form of a two-dimensional map or image.

5. The method of claim 4 wherein the NMR data acquired in step b. is a decaying signal dependent on the relaxation parameter $T_2$.

6. The method of claim 5 wherein the parameter extracted in step d. is selected from the group consisting of the NMR relaxation parameter $T_1$, the NMR relaxation parameter $T_2$ and the molecular diffusion coefficient.

7. The method of claim 6 wherein the variable in step e. is selected in order that the detected NMR signal depends on a NMR parameter selected from the group consisting of NMR relaxation parameter $T_1$, NMR relaxation parameter $T_2$ and the molecular diffusion coefficient.

8. The method of claim 7 wherein the data obtained from step e. depends on one or more of the NMR parameters from the group consisting of the NMR relaxation parameter $T_1$, the NMR relaxation parameter $T_2$ and the molecular diffusion coefficient.

9. The method of claim 6 wherein the variable in step e. is selected from the group consisting of NMR pulse sequence timings, NMR pulse sequence magnetic field gradients and combinations thereof.

10. The method of claim 1 further comprising further repeating step c. to 3 more dimensions.

11. The method of claim 1 wherein the porous medium is selected from the group consisting of rock, reservoir rock and subterranean rock.

12. The method of claim 11 further comprising using the extracted parameters to determine the content of pores in the porous medium.

13. The method of claim 11 further comprising using the extracted parameters to determine the content of pores in the porous medium.

\* \* \* \* \*